(12) United States Patent
Dippe et al.

(10) Patent No.: US 9,803,180 B2
(45) Date of Patent: Oct. 31, 2017

(54) S-ADENOSYLMETHIONINE (SAM) SYNTHASE VARIANTS FOR THE SYNTHESIS OF ARTIFICIAL COFACTORS

(71) Applicant: LEIBNIZ-INSTITUT FUR PFLANZENBIOCHEMIE STIFTUNG DES OFFENTLICHEN RECHTS, Halle (Saale) (DE)

(72) Inventors: Martin Dippe, Halle (DE); Wolfgang Brandt, Halle (DE); Ludger A. Wessjohann, Halle (DE); Hannes Rost, Halle (DE); Andrea Porzel, Halle (DE)

(73) Assignee: LEIBNIZ-INSTITUT FÜR PFLANZENBIOCHEMIE STIFTUNG DES ÖFFENTLICHEN RECHTS, Halle (Saale) (DE)

( * ) Notice: Subject to any disclaimer, the term of this patent is extended or adjusted under 35 U.S.C. 154(b) by 0 days.

(21) Appl. No.: 15/034,773

(22) PCT Filed: Sep. 4, 2014

(86) PCT No.: PCT/EP2014/002398
§ 371 (c)(1),
(2) Date: May 5, 2016

(87) PCT Pub. No.: WO2015/067331
PCT Pub. Date: May 14, 2015

(65) Prior Publication Data
US 2016/0264946 A1 Sep. 15, 2016
US 2017/0240870 A9 Aug. 24, 2017

(30) Foreign Application Priority Data

Nov. 6, 2013 (EP) .................................... 13005228

(51) Int. Cl.
*C12N 9/12* (2006.01)
*C12N 9/10* (2006.01)
*C12P 19/40* (2006.01)

(52) U.S. Cl.
CPC ............ *C12N 9/1085* (2013.01); *C12P 19/40* (2013.01); *C12Y 205/01006* (2013.01)

(58) Field of Classification Search
None
See application file for complete search history.

(56) References Cited

U.S. PATENT DOCUMENTS 6,312,920 B1  11/2001  DeHoff et al.

FOREIGN PATENT DOCUMENTS

| EP | 1659174 A2 | 5/2006 |
| EP | 2071022 A1 | 6/2009 |
| WO | 03008591 A1 | 1/2003 |

OTHER PUBLICATIONS

Markham, et al., "Structure-function relationships in methionine adenosyltransferases," Celular and Molecular Life Sciences, 2009, vol. 66, No. 4, pp. 636-648.
International Search Report and Written Opinion issued in PCT/EP2014/002398, dated Dec. 22, 2014 (12 pages).
Second Written Opinion issued in PCT/EP2014/002398, dated Sep. 14, 2015 (7 pages).
Third Written Opinion issued in PCT/EP2014/002398, dated Nov. 6, 2015 (7 pages).
International Preliminary Report on Patentability issued for PCT/EP2014/002398, dated Jan. 29, 2016 (11 pages).

*Primary Examiner* — Richard Hutson
(74) *Attorney, Agent, or Firm* — Armstrong Teasdale LLP

(57) ABSTRACT

The present invention relates to isolated polypeptides that are derived from wildtype *Bacillus subtilis* S-Adenosylmethionine (SAM) synthase or from a biologically active fragment thereof, wherein said isolated polypeptides comprise an amino acid sequence that, in relation to the amino acid sequence of said wildtype *Bacillus subtilis* SAM synthase or of the biologically active fragment thereof, comprises at least one amino acid substitution, selected from the group consisting of amino acid substitutions at positions I317 and I105. The present invention further relates to respective isolated nucleic acids, vectors, host cells, uses and methods for the production of SAM derivatives.

6 Claims, 7 Drawing Sheets

S-ADENOSYLMETHIONINE (SAM) SYNTHASE VARIANTS FOR THE SYNTHESIS OF ARTIFICIAL COFACTORS

CROSS-REFERENCE TO RELATED APPLICATIONS

This application is a U.S. National Phase patent application of International Application Serial Number PCT/EP2014/002398, filed on Sep. 4, 2014, which is hereby incorporated by reference in its entirety, and which claims the benefit of European Patent Application Number 13005228.5, filed on Nov. 6, 2013, which is hereby incorporated by reference in its entirety.

STATEMENT IN SUPPORT OF FILING A SEQUENCE LISTING

The instant application contains a Sequence Listing. A paper copy of the Sequence Listing and a computer readable copy of the Sequence Listing in ASCII format are provided herein and are herein incorporated by reference in their entirety. Said computer readable copy, created on Apr. 21, 2016, is named "23311777_1.txt" and is 24,918 bytes in size (as measured in MICROSOFT WINDOWS® EXPLORER). This Sequence Listing consists of SEQ ID NOs: 1-7.

BACKGROUND OF THE DISCLOSURE

The present invention relates to isolated polypeptides that are derived from wildtype *Bacillus subtilis* S-Adenosylmethionine (SAM) synthase or from a biologically active fragment thereof, wherein said isolated polypeptides comprise an amino acid sequence that, in relation to the amino acid sequence of said wildtype *Bacillus subtilis* SAM synthase or of the biologically active fragment thereof, comprises at least one amino acid substitution, selected from the group consisting of amino acid substitutions at positions I317 and I105. The present invention further relates to respective isolated nucleic acids, vectors, host cells, uses and methods for the production of SAM derivatives.

Almost all enzyme-catalyzed methyl transfer reactions depend on the cofactor S-adenosylmethionine (SAM). Thus, availability of this compound is crucial for application of the corresponding methyltransferases in biotechnology, e.g. in the production of valuable fine chemicals and pharmaceuticals. In cellular metabolism, this universal methyl donor is formed by adenosylation of L-methionine by SAM synthases (SAMS). However, enzymatic synthesis of SAM is not feasible for industrial application due to inhibition of most SAMS by their product SAM which results in stagnating conversion, low yield or—in life whole-cell biocatalysts—in insufficient availability of the cofactor. In addition, most SAMS enzymes does not tolerate changes in the structure of their amino acid substrate. Thus, these enzymes lack the ability to synthesize cofactor analogues from artificial methionine derivatives. From the large number of SAMS enzymes which have been characterized, only two proteins tolerably convert S-ethyl-L-homocysteine (ethionine) to S-adenosylethionine. However, these proteins are not feasible for the synthesis of SAM derivatives which enable transfer of non-natural long-chain or functionalized alkyl groups.

BRIEF SUMMARY OF THE DISCLOSURE

Accordingly, the technical problem underlying the present invention is to provide variants of SAM synthase that can be used for the biocatalytic production of SAM and SAM analogues having artificial alkyl chains or allyl chains, or chains of the type $-(CH_2)_n-OR$, $-(CH_2)_n-SR$, or $-(CH_2)_n-Hal$, wherein n is 1 to 3, R is an alkyl, preferably a $C_1$ to $C_4$ alkyl, and Hal is a halogen, preferably on an industrial scale, wherein said variants should display a broad substrate specificity, high catalytic efficiency and reduced product inhibition as compared to conventional SAM synthases.

The solution to the above technical problem is achieved by the embodiments characterized in the claims.

BRIEF DESCRIPTION OF THE DRAWINGS

FIG. 1 shows a SDS-PAGE of purified SAM synthase from *Bacillus subtilis* (lane 1) and its variants I317V (lane 2), I317A (lane 3), I105V/I317A (lane 4), I105A/I317A (lane 5), I105V/I317S (lane 6) and I105S/I317S (lane 7).

FIG. 2A shows the tertiary structure of the tetramer with SAM (space fill representations) bound between two monomer units. FIG. 2B shows the active site with the bound product SAM. The space for docking of SAM derivatives with larger functional groups R is restricted by the two isoleucines I105 and I317 which were therefore subject of site-directed mutagenesis. FIG. 2C shows the arrangement of the substrate analogues S-n-butyl-L-homocysteine and adenylyl imidodiphosphate in the active center. The arrows indicate the nucleophilic attack (short arrow) during catalysis. The reaction is accompanied with conformational change of the protein which will lead to steric hindrance (long arrow) with the amino acid side chain.

FIGS. 3A-3E show the rates of conversion of amino acid substrates catalyzed by the SAMS enzyme from *Bacillus subtilis* (FIG. 3A) and its variants I317V (FIG. 3B), I317A (FIG. 3C), I105V/I317A (FIG. 3D) or I105A/I317A (FIG. 3E) as a function of the substrate concentration. The reaction with L-methionine (open circles), D,L-methionine (closed circles), D,L-methionine-(methyl-D3) (x), D,L-ethionine (hatched circles), S-n-propyl-D,L-homocysteine (open triangles), S-n-butyl-D,L-homocysteine (closed triangles) or S-(2-methylvinyl)-D,L-homocysteine (diamonds) was assessed by spectrophotometric determination of phosphate which is released from the co-substrate ATP during the reaction.

FIGS. 4A-4C show the formation of SAM and SAM derivatives by the SAM synthase enzyme from *Bacillus subtilis* (FIG. 4A) or its variants I317V (FIG. 4B) and I317A (FIG. 4C). The conversion of the L-enantiomer of methionine (closed circles), ethionine (hatched circles), S-n-propylhomocysteine (open triangles) and S-n-butylhomocysteine (closed triangles) from the corresponding racemic amino acid (10 mM) was performed in the presence of equal amounts of enzyme (10 mU ml$^{-1}$). The reactions were analyzed by HPTLC.

DETAILED DESCRIPTION OF THE DISCLOSURE

Figure 1:
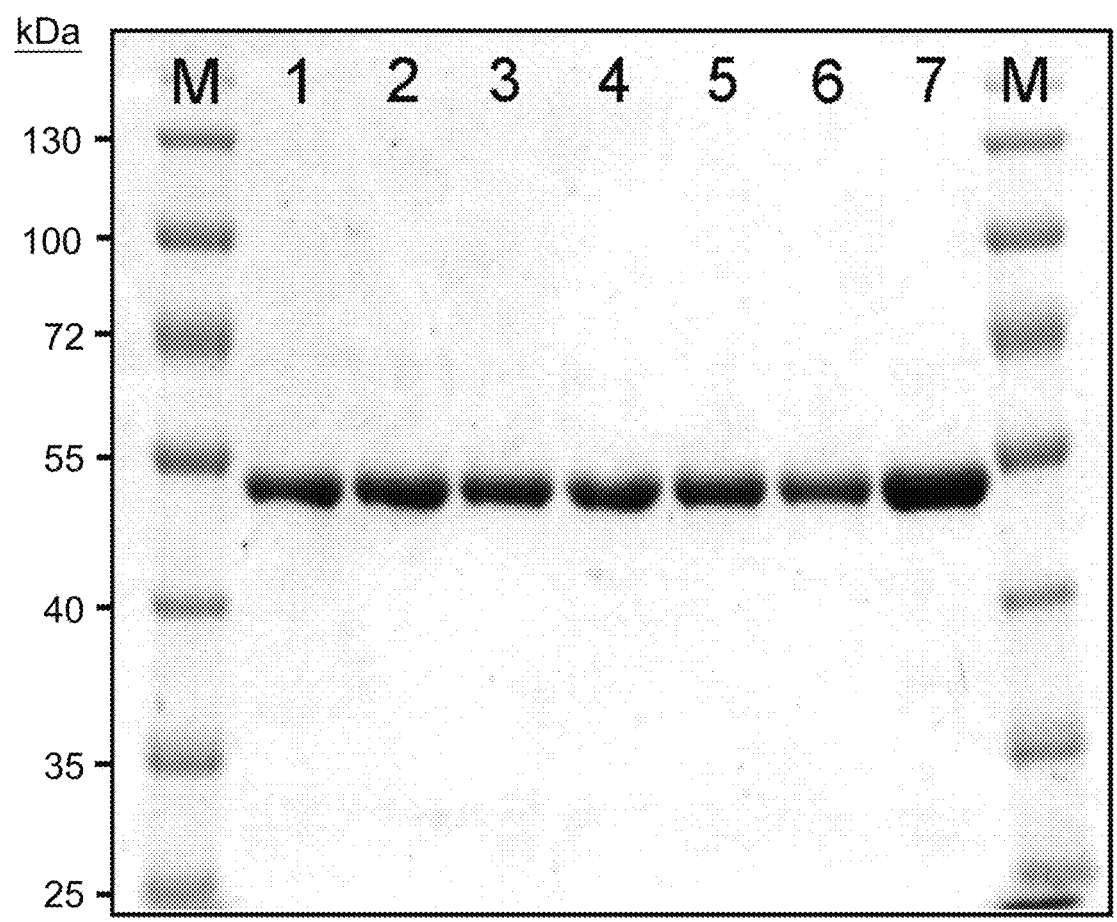
FIG. 1: SAM Synthase Enzymes

In particular, in a first aspect, the present invention relates to an isolated polypeptide derived from wildtype *Bacillus subtilis* S-Adenosylmethionine (SAM) synthase or from a biologically active fragment thereof, wherein said isolated polypeptide comprises an amino acid sequence that, in relation to the amino acid sequence of said wildtype *Bacillus subtilis* SAM synthase (SEQ ID NO: 1) or of the biologically active fragment thereof, comprises at least one amino acid substitution, selected from the group consisting of amino acid substitutions at positions I317 and I105. In particular, the isolated polypeptide of the present invention can have any amino acid substitution at position I317, at position I105, or at both positions I317 and I105, wherein an amino acid substitution at position I317, or at both positions I317 and I105 is particularly preferred. The substitute amino acid is not particularly limited and can be any proteinogenic amino acid with the obvious exception of isoleucine (I). However, preferably the substitute amino acid is an amino acid that is less spacious, i.e. less voluminous than isoleucine. Particularly preferred amino acids in this respect are glycine (G), leucine (L), proline (P), threonine (T), cysteine (C), serine (S), aspartic acid (D), glutamic acid (E), asparagine (N), valine (V), and alanine (A), wherein valine (V), and alanine (A) are most preferred.

Thus, in a particularly preferred embodiment, the present invention relates to an isolated polypeptide derived from wildtype *Bacillus subtilis* S-Adenosylmethionine (SAM) synthase or from a biologically active fragment thereof, wherein said isolated polypeptide comprises an amino acid sequence that, in relation to the amino acid sequence of said wildtype *Bacillus subtilis* SAM synthase (SEQ ID NO: 1) or of the biologically active fragment thereof, comprises at least one amino acid substitution, selected from the group consisting of the amino acid substitutions I317G, I317L, I317P, I317T, I317C, I317D, I317E, I317N, I317A and I317V.

In another particularly preferred embodiment, the present invention relates to an isolated polypeptide derived from wildtype *Bacillus subtilis* S-Adenosylmethionine (SAM) synthase or from a biologically active fragment thereof, wherein said isolated polypeptide comprises an amino acid sequence that, in relation to the amino acid sequence of said wildtype *Bacillus subtilis* SAM synthase (SEQ ID NO: 1) or of the biologically active fragment thereof, comprises at least one amino acid substitution, selected from the group consisting of the amino acid substitutions I317A and I317V.

In this context, the term "polypeptide derived from wildtype *Bacillus subtilis* SAM synthase or from a biologically active fragment thereof" as used herein is intended to relate to polypeptides that essentially correspond to wildtype *Bacillus subtilis* SAM synthase, provided that in relation to said wildtype *Bacillus subtilis* SAM synthase they comprise at least one of the amino acid substitutions defined above. Further, said term is intended to relate to polypeptides that can comprise any number of additional amino acid substitutions, additions, or deletions, provided that the resulting polypeptide retains the biological activity of a SAM synthase. In this context, the term "retains the biological activity of a SAM synthase" as used herein, as well as the term "biologically active fragment thereof" as used herein, relates to polypeptides that have at least 0.1%, at least 0.5%, at least 1%, at least 5%, at least 10%, at least 25%, at least 50%, preferably at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 97.5%, at least 98%, at least 98.5%, at least 99%, at least 99.5%, 100%, or more than 100% of the activity of wildtype *Bacillus subtilis* SAM synthase, as determined in a standard SAM synthase activity assay known in the art.

While the number of additional amino acid substitutions, additions, or deletions is generally only limited by the above proviso concerning the biological activity of the resulting polypeptide, it is preferable that the resulting polypeptide has at least 50%, at least 52.5%, at least 55%, at least 57.5%, at least 60%, at least 62.5%, at least 65%, at least 67.5%, at least 70%, at least 72.5%, at least 75%, at least 76.25%, at least 77.5%, at least 78.75%, at least 80%, at least 81.25%, at least 83.75%, at least 85%, at least 86.25%, at least 87.5%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.25%, at least 95.5%, at least 95.75%, at least 96%, at least 96.25%, at least 96.5%, at least 96.75%, at least 97%, at least 97.25%, at least 97.5%, at least 97.75%, at least 98%, at least 98.25%, at least 98.5%, at least 98.75%, at least 99%, at least 99.25%, at least 99.5%, or 99.75% identity to wildtype *Bacillus subtilis* SAM synthase.

Further, the terms "an amino acid sequence that, in relation to the amino acid sequence of said wildtype *Bacillus subtilis* SAM synthase (SEQ ID NO: 1) or of the biologically active fragment thereof, comprises at least one amino acid substitution, selected from the group consisting of amino acid substitutions at positions I317 and I105" and "an amino acid sequence that, in relation to the amino acid sequence of said wildtype *Bacillus subtilis* SAM synthase (SEQ ID NO: 1) or of the biologically active fragment thereof, comprises at least one amino acid substitution, selected from the group consisting of the amino acid substitutions I317A and I317V" as used herein are intended to relate to a respective amino acid sequence, i.e. an amino acid sequence that (i) essentially corresponds to the amino acid sequence of said wildtype *Bacillus subtilis* SAM synthase (SEQ ID NO: 1), (ii) in relation to said sequence comprises at least one of the above amino acid substitutions, and (iii) can comprise any further amino acid substitutions, additions or deletions as defined above, wherein the number of said further amino acid substitutions, additions or deletions is also as defined above with respect to the biological activity of the resulting polypeptide, preferably with respect to the identity of the resulting polypeptide to wildtype *Bacillus subtilis* SAM synthase.

In a further embodiment, the isolated polypeptide of the present invention further comprises an amino acid substitution, selected from the group consisting of the amino acid substitutions I105G, I105L, I105P, I105T, I105C, I105S, I105A and I105V.

Preferably, in a further embodiment, the isolated polypeptide of the present invention further comprises an amino acid substitution, selected from the group consisting of the amino acid substitutions I105A and I105V.

In a preferred embodiment, the isolated polypeptide of the present invention comprises the amino acid sequence of SEQ ID NO: 2, said amino acid sequence containing the amino acid substitution I317A in relation to the amino acid sequence of wildtype *Bacillus subtilis* SAM synthase (SEQ ID NO: 1). Even more preferably, the isolated polypeptide of the present invention consists of the amino acid sequence of SEQ ID NO: 2.

In a further preferred embodiment, the isolated polypeptide of the present invention comprises the amino acid sequence of SEQ ID NO: 3, said amino acid sequence containing the amino acid substitution I317V in relation to the amino acid sequence of wildtype *Bacillus subtilis* SAM synthase (SEQ ID NO: 1). Even more preferably, the isolated polypeptide of the present invention consists of the amino acid sequence of SEQ ID NO: 3.

In a further preferred embodiment, the isolated polypeptide of the present invention comprises the amino acid sequence of SEQ ID NO: 4, said amino acid sequence containing the amino acid substitutions I317A and I105A in relation to the amino acid sequence of wildtype *Bacillus subtilis* SAM synthase (SEQ ID NO: 1). Even more preferably, the isolated polypeptide of the present invention consists of the amino acid sequence of SEQ ID NO: 4.

In a further preferred embodiment, the isolated polypeptide of the present invention comprises the amino acid sequence of SEQ ID NO: 5, said amino acid sequence containing the amino acid substitutions I317V and I105A in relation to the amino acid sequence of wildtype *Bacillus subtilis* SAM synthase (SEQ ID NO: 1). Even more preferably, the isolated polypeptide of the present invention consists of the amino acid sequence of SEQ ID NO: 5.

In a further preferred embodiment, the isolated polypeptide of the present invention comprises the amino acid sequence of SEQ ID NO: 6, said amino acid sequence containing the amino acid substitutions I317A and I105V in relation to the amino acid sequence of wildtype *Bacillus subtilis* SAM synthase (SEQ ID NO: 1). Even more preferably, the isolated polypeptide of the present invention consists of the amino acid sequence of SEQ ID NO: 6.

In a further preferred embodiment, the isolated polypeptide of the present invention comprises the amino acid sequence of SEQ ID NO: 7, said amino acid sequence containing the amino acid substitutions I317V and I105V in relation to the amino acid sequence of wildtype *Bacillus subtilis* SAM synthase (SEQ ID NO: 1). Even more preferably, the isolated polypeptide of the present invention consists of the amino acid sequence of SEQ ID NO: 7.

In a further aspect, the present invention relates to an isolated nucleic acid encoding a polypeptide according to the present invention. Such nucleic acids are not particularly limited and can be single-stranded or double-stranded DNA molecules, RNA molecules, DNA/RNA hybrid molecules or artificial and/or modified nucleic acid molecules. The term "nucleic acid encoding a polypeptide according to the present invention" as used herein is intended to relate to nucleic acid molecules comprising the coding sequence of the respective polypeptide, as well as nucleic acid molecules comprising a sequence that is fully complementary to the coding sequence of the respective polypeptide.

In a further aspect, the present invention relates to a vector comprising the nucleic acid according to the present invention. Suitable vectors are not particularly limited and are known in the art. They include for example plasmid vectors, e.g. well known expression vectors, in particular bacterial expression vectors such as pET28a(+), viral vectors, cosmid vectors and artificial chromosomes.

In yet another aspect, the present invention relates to a host cell comprising the nucleic acid according to the present invention or the vector according to the present invention. Suitable host cells are not particularly limited and are known in the art. They include for example bacterial cells, e.g. well known bacterial cells for recombinant protein expression such as cells based on the *E. coli* strain K12, e.g. *E. coli* BL21 (DE3), gram-positive bacterial cells such as *Bacillus subtilis*, but also yeast cells, insect cells, plant cells, and mammalian cells.

In a further aspect, the present invention relates to a method for the biocatalytic generation of S-Adenosylmethionine (SAM) and/or SAM analogues having artificial alkyl chains or allyl chains, or chains of the type —$(CH_2)_n$—OR, —$(CH_2)_n$—SR, or —$(CH_2)_n$—Hal, wherein n is 1 to 3, R is an alkyl, preferably a $C_1$ to $C_4$ alkyl, and Hal is a halogen, comprising the step of reacting a suitable S-alkyl homocysteine, S-methylvinyl homocysteine, or other homocysteine derivative with a polypeptide of the present invention.

SAM analogues that can be generated with the method of the present invention are not particularly limited, depending only on the substrate specificity of the SAM synthase variant used and the selected starting product. Examples include S-adenosylethionine generated from S-ethyl-L-homocysteine, S-adenosylpropionine generated from S-n-propyl-D,L-homocysteine, S-adenosyl buthionine generated from S-n-butyl-D, L-homocysteine, and S-adenosyl-S-methylvinyl homocysteine from S-methylvinyl-D,L-homocysteine.

In a final aspect, the present invention relates to the use of a polypeptide according to the present invention for the generation of S-Adenosylmethionine (SAM) and/or SAM analogues having artificial alkyl chains or allyl chains, or chains of the type —$(CH_2)_n$—OR, —$(CH_2)_n$—SR, or —$(CH_2)_n$—Hal, wherein n is 1 to 3, R is an alkyl, preferably a $C_1$ to $C_4$ alkyl, and Hal is a halogen. In this aspect, SAM analogues that can be generated and their respective starting products are as defined above for the method of the present invention.

The present invention provides SAM synthase variants that can be advantageously used in the generation of SAM and SAM analogues, in particular on an industrial scale. The SAM synthase variants according to the present invention can be highly expressed in suitable host cells and are characterized by a high productivity, a broad substrate specificity for a wide range of starting products resulting in a broad range of SAM analogues that can be generated, and a reduced product inhibition. These characteristics make the SAM synthase variants according to the present invention ideal candidates for the large-scale generation of SAM and SAM analogues in an industrial setting.

To obtain a SAMS enzyme suitable for biocatalytic production of SAM and analogues, the protein from *Bacillus subtilis* was improved by rational protein design. Substitution of two conserved isoleucine residues (I105 and I317) located in close proximity to the active site extended the substrate spectrum of the enzyme to artificial methionine derivatives. An introduction of a less spacious valine or alanine residue into position 105 and 317 led to variants which were able to convert methionine and S-alkylhomocysteines bearing substituents with 2 to 4 carbon atoms. In contrast to the wild-type enzyme, the variants I317V and I317A were much less affected by product inhibition and proved to be favorable for the preparative synthesis of SAM and its long-chain analogues. In addition, these variants might be applied to generate a high-level intracellular concentration of SAM in prokaryotic hosts upon addition of methionine to the growth medium.

The present invention discloses the following amino acid sequences.

```
wildtype Bacillus subtilis SAM synthase
(SEQ ID NO: 1)
msknrrlfts esvteghpdk icdqisdsil deilkkdpna rvacetsvtt glvlvsgeit tstyvdipkt vrqtikeigy trakygfdae tcavltside qsadiamgvd qalearegtm sdeeieaiga gdqglmfgya cnetkelmpl pislahklar rlsevrkedi lpylrpdgkt qvtveydenn kpvridaivi
``` stqhhpeitl eqiqrnikeh vinpvvpeel ideetkyfin ptgrfviggp qgdagltgrk iivdtyggya rhgggafsgk datkvdrsaa yaaryvakni vaaeladsce vqlayaigva qpvsisintf gsgkaseekl ievvrnnfdl rpagiikmld lrrpiykqta ayghfgrhdv dlpwertdka eqlrkealge I317A SAM synthase variant (SEQ ID NO: 2)
msknrrlfts esvteghpdk icdqisdsil deilkkdpna rvacetsvtt glvlvsgeit tstyvdipkt vrqtikeigy trakygfdae tcavltside qsadiamgvd qalearegtm sdeeieaiga gdqglmfgya cnetkelmpl pislahklar rlsevrkedi lpylrpdgkt qvtveydenn kpvridaivi stqhhpeitl eqiqrnikeh vinpvvpeel ideetkyfin ptgrfviggp qgdagltgrk iivdtyggya rhgggafsgk datkvdrsaa yaaryvakni vaaeladsce vqlayaagva qpvsisintf gsgkaseekl ievvrnnfdl rpagiikmld lrrpiykqta ayghfgrhdv dlpwertdka eqlrkealge I317V SAM synthase variant (SEQ ID NO: 3)
msknrrlfts esvteghpdk icdqisdsil deilkkdpna rvacetsvtt glvlvsgeit tstyvdipkt vrqtikeigy trakygfdae tcavltside qsadiamgvd qalearegtm sdeeieaiga gdqglmfgya cnetkelmpl pislahklar rlsevrkedi lpylrpdgkt qvtveydenn kpvridaivi stqhhpeitl eqiqrnikeh vinpvvpeel ideetkyfin ptgrfviggp qgdagltgrk iivdtyggya rhgggafsgk datkvdrsaa yaaryvakni vaaeladsce vqlayavgva qpvsisintf gsgkaseekl ievvrnnfdl rpagiikmld lrrpiykqta ayghfgrhdv dlpwertdka eqlrkealge I105A/I317A SAM synthase variant (SEQ ID NO: 4)
msknrrlfts esvteghpdk icdqisdsil deilkkdpna rvacetsvtt glvlvsgeit tstyvdipkt vrqtikeigy trakygfdae tcavltside qsadaamgvd qalearegtm sdeeieaiga gdqglmfgya cnetkelmpl pislahklar rlsevrkedi lpylrpdgkt qvtveydenn kpvridaivi stqhhpeitl eqiqrnikeh vinpvvpeel ideetkyfin ptgrfviggp qgdagltgrk iivdtyggya rhgggafsgk datkvdrsaa yaaryvakni vaaeladsce vqlayaagva qpvsisintf gsgkaseekl ievvrnnfdl rpagiikmld lrrpiykqta ayghfgrhdv dlpwertdka eqlrkealge I105A/I317V SAM synthase variant (SEQ ID NO: 5)
msknrrlfts esvteghpdk icdqisdsil deilkkdpna rvacetsvtt glvlvsgeit tstyvdipkt vrqtikeigy trakygfdae tcavltside qsadaamgvd qalearegtm sdeeieaiga gdqglmfgya cnetkelmpl pislahklar rlsevrkedi lpylrpdgkt qvtveydenn kpvridaivi stqhhpeitl eqiqrnikeh vinpvvpeel ideetkyfin ptgrfviggp qgdagltgrk iivdtyggya rhgggafsgk datkvdrsaa yaaryvakni vaaeladsce vqlayavgva qpvsisintf gsgkaseekl ievvrnnfdl rpagiikmld lrrpiykqta ayghfgrhdv dlpwertdka eqlrkealge I105V/I317A SAM synthase variant (SEQ ID NO: 6)
msknrrlfts esvteghpdk icdqisdsil deilkkdpna rvacetsvtt glvlvsgeit tstyvdipkt vrqtikeigy trakygfdae tcavltside qsadvamgvd qalearegtm sdeeieaiga gdqglmfgya cnetkelmpl pislahklar rlsevrkedi lpylrpdgkt qvtveydenn kpvridaivi stqhhpeitl eqiqrnikeh vinpvvpeel ideetkyfin ptgrfviggp qgdagltgrk iivdtyggya rhgggafsgk datkvdrsaa yaaryvakni vaaeladsce vqlayaagva qpvsisintf gsgkaseekl ievvrnnfdl rpagiikmld lrrpiykqta ayghfgrhdv dlpwertdka eqlrkealge I105V/I317V SAM synthase variant (SEQ ID NO: 7)
msknrrlfts esvteghpdk icdqisdsil deilkkdpna rvacetsvtt glvlvsgeit tstyvdipkt vrqtikeigy trakygfdae tcavltside qsadvamgvd qalearegtm sdeeieaiga gdqglmfgya cnetkelmpl pislahklar rlsevrkedi lpylrpdgkt qvtveydenn kpvridaivi stqhhpeitl eqiqrnikeh vinpvvpeel ideetkyfin ptgrfviggp qgdagltgrk iivdtyggya rhgggafsgk datkvdrsaa yaaryvakni vaaeladsce vqlayavgva qpvsisintf gsgkaseekl ievvrnnfdl rpagiikmld lrrpiykqta ayghfgrhdv dlpwertdka eqlrkealge The present invention will be further illustrated in the following examples without being limited thereto.

EXAMPLES

Example 1

Recombinant Expression of Wildtype *Bacillus subtilis* SAM Synthase

Figure 3A:
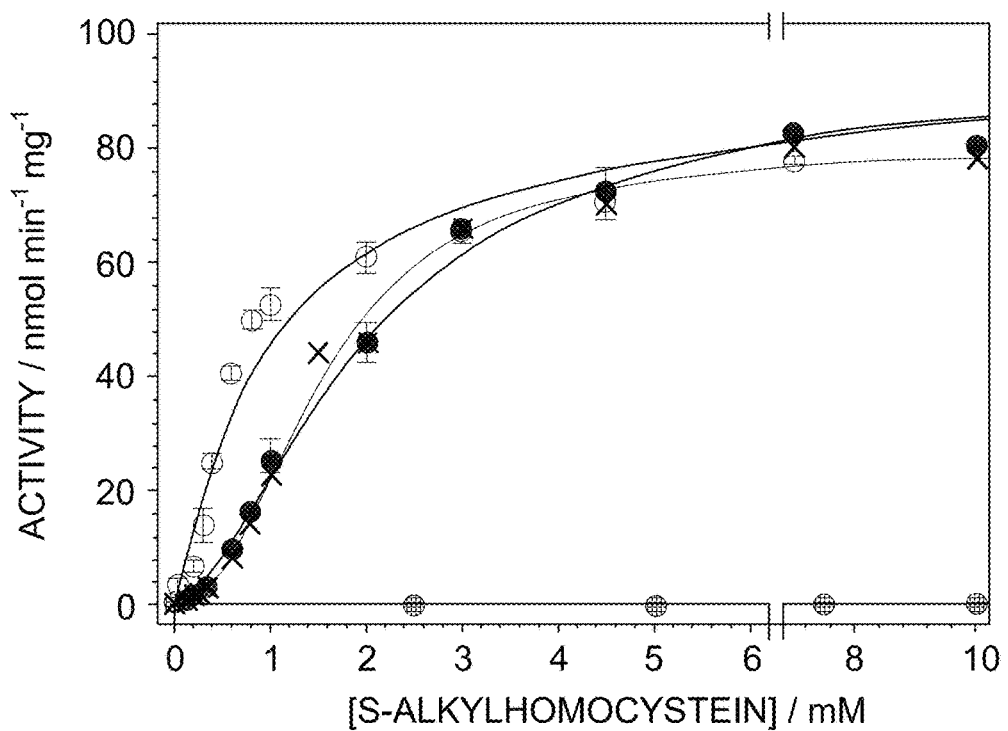
FIGS. 3A-3E: Conversion of Methionine and Derivatives

To address the problem of availability of the cofactor S-adenosyl-L-methionine (SAM) in *Escherichia coli*, an enhancement of endogenous SAM synthesis was envisioned. Therefore, the SAM synthase gene from *Bacillus subtilis* was cloned into the vector pET28a(+) and introduced in *E. coli* BL21 (DE3). Purified enzyme (FIG. 1, lane 1) could be obtained in high yields (59 mg/l of culture). Since the protein is not inhibited by the D-enantiomer of methionine (FIG. 3A), even inexpensive racemic mixtures of this amino acid can be used as substrate.

Example 2

Generation and Characterization of SAM Synthase Variants

Beside regeneration of the natural cofactor SAM, recombinant SAM synthase variants (FIG. 1, lanes 2 to 7) were applied for the synthesis of cofactor analogues having artificial alkyl chains.

For these studies, a series of S-alkylhomocysteines with linear (D,L-methionine-(methyl-D3), -ethionine, -propionine and -buthionine), branched (D,L-isopropionine and -isobuthionines), unsaturated (D,L-methylvinylhomocysteine) and functionalized (D,L-hydroxyethionine and -carboxymethionine) alkyl groups were synthesized from D,L-homocysteine thiolactone and tested for conversion by the cloned (wildtype) SAM synthase. However, the enzyme did not accept any of these methionine derivatives.

Figure 2A:
FIGS. 2A-2C: Model of the SAM Synthase from *Bacillus subtilis*
Figure 2B:
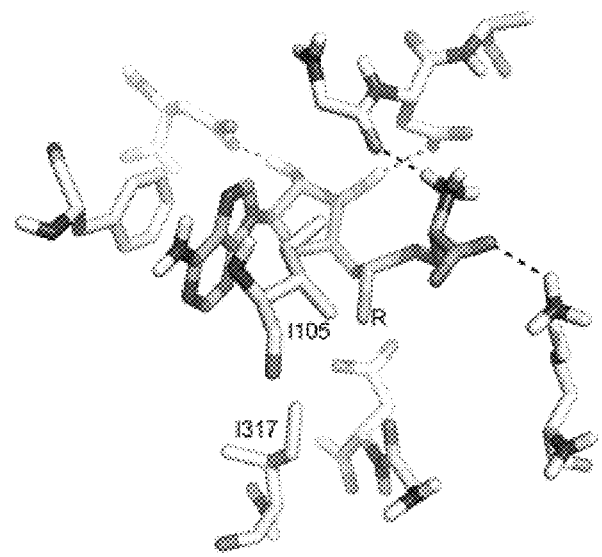
Figure 2C:
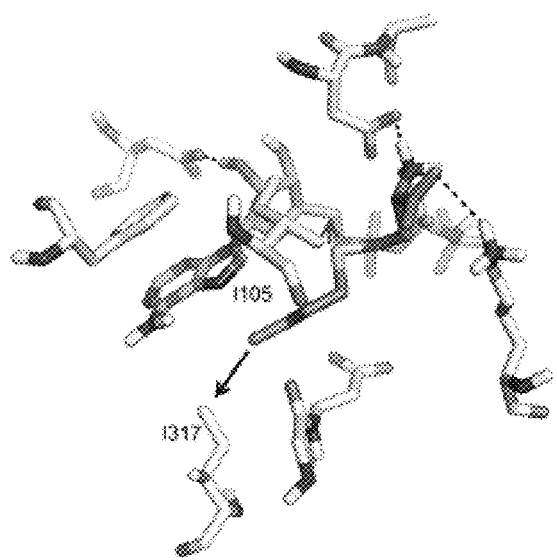
Figure 3B:
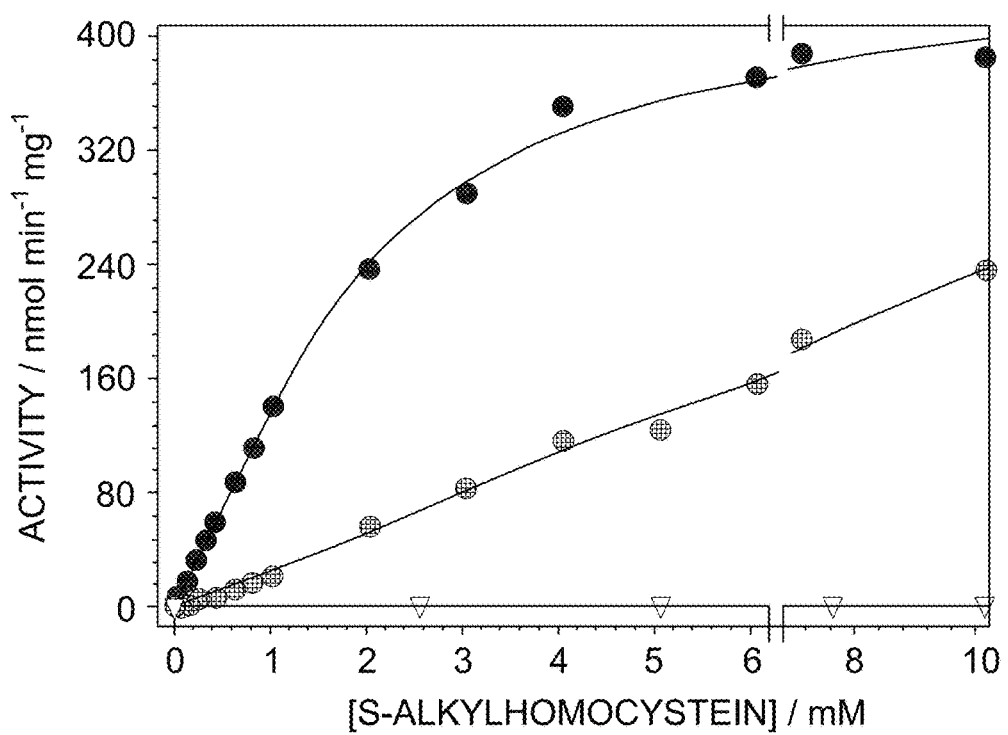
Figure 3C:
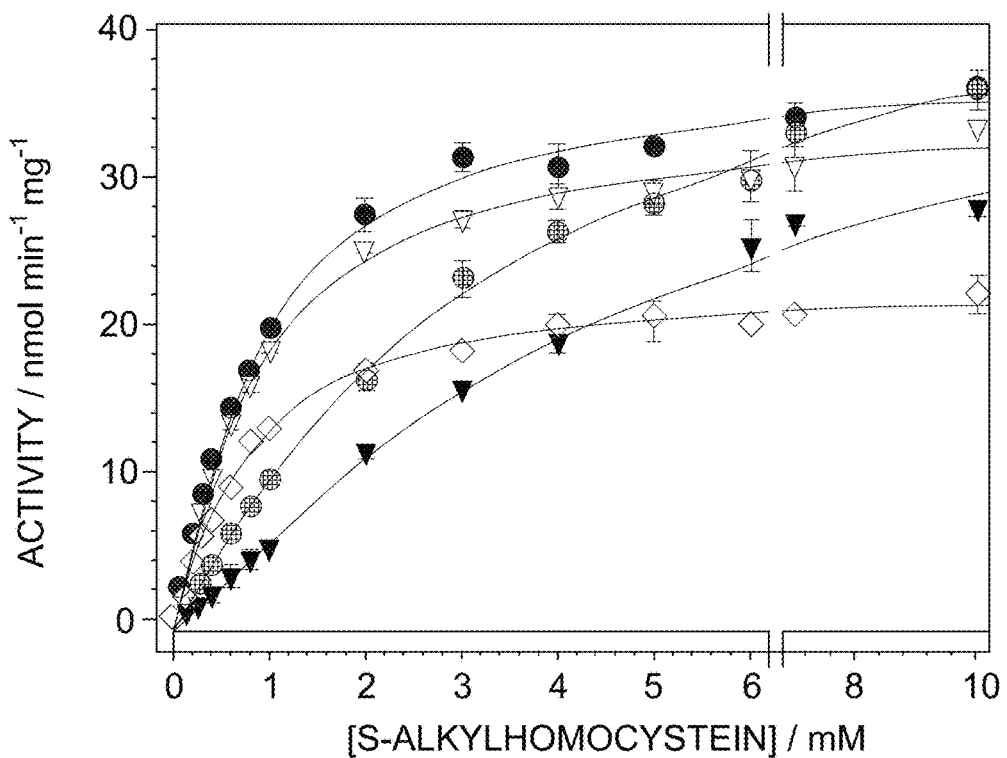
Figure 3D:
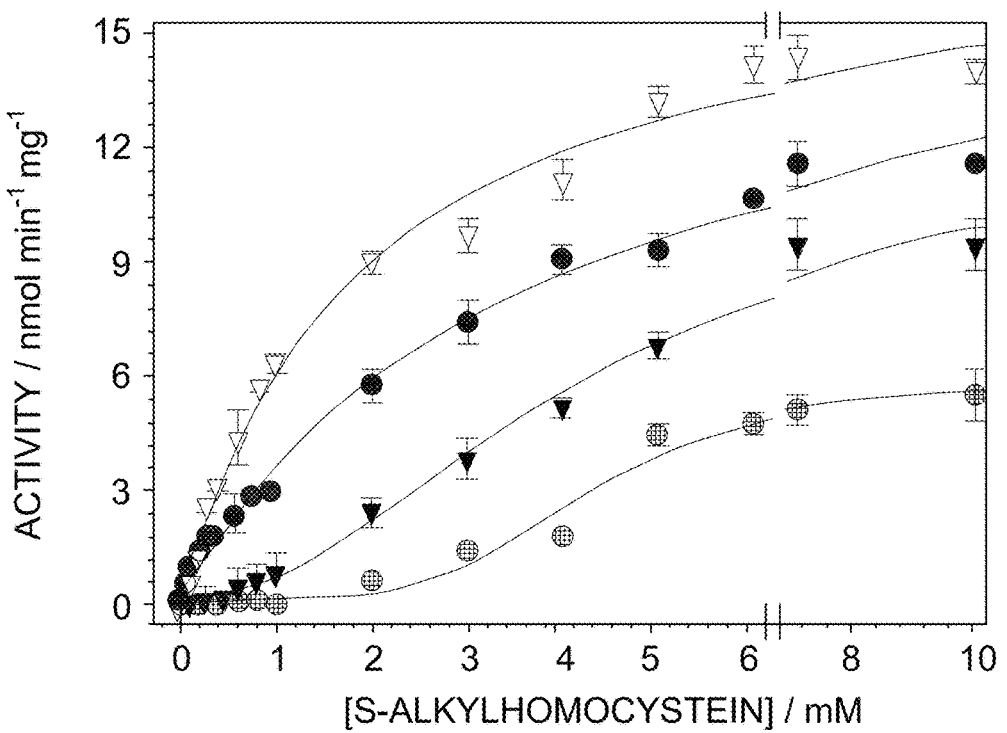

As derived from a homology model which is based on the crystal structure of the protein from *E. coli* (PDB code 1XRA), a hydrophobic cleft formed from two conserved isoleucine residues hinders the generation of cofactor analogues from amino acid substrates with bulky alkyl residues (FIG. 2). Accordingly, both residues were exchanged against less voluminous amino acids by site-directed mutagenesis. Especially I317 proved to be crucial for substrate selectivity. In addition to methionine, the variant I317V also converts ethionine (FIG. 3B). If I317 is substituted by an even smaller alanine residue, the corresponding variant is active on ethionine, propionine, buthionine and the unsaturated D,L-methylvinylhomocysteine (FIG. 3C). Finally, an exchange of both isoleucines to alanine results in acceptance of the artificial long-chain substrates only (FIG. 3D).

Example 3

Production of SAM Derivatives by SAM Synthase Variants

Due to their broad substrate spectrum, the variants I317V and I317A were used for the production of the SAM derivatives S-adenosylethionine, -propionine, -buthionine and -S-methylvinylhomocysteine in preparative scale. The compounds were synthesized from 0.2 mmol of D,L-amino acid and purified by cation exchange chromatography on SP-Sephadex C-25. Yields ranged from 10 to 52%, related to the L-form of the amino acid. As tested by enzymatic conversion of produced SAM by catechol-O-methyltransferase, the preparations contained the biological active form of the cofactor (80 to 92% of total SAM).

Example 4

Characterization of Further SAM Synthase Variants

The influence of position 317 on catalytic turnover and its crucial role in determination of substrate spectrum was additionally confirmed by introduction of other small- and medium-sized amino acid residues. Enzymes substituted for aliphatic (I317G, I317P, I317L) or polar (I317E, I317D, I317N) amino acids showed a strongly reduced activity ($\geq 5.4$ nmol min$^{-1}$ mg$^{-1}$). On the other hand, substitution by cysteine resulted in a tolerably active enzyme which—similar to the variant I317A-converted methionine and homologs ($59.4 \pm 0.4$, $16.4 \pm 0.7$, $8.4 \pm 0.3$ and $6.0 \pm 0.3$ nmol min$^{-1}$ mg$^{-1}$ for conversion of 5 mM D,L-methionine, -ethionine, -propionine and -buthionine, respectively).

Example 5

Characterization of Double Mutant SAM Synthase Variants

Figure 3E:
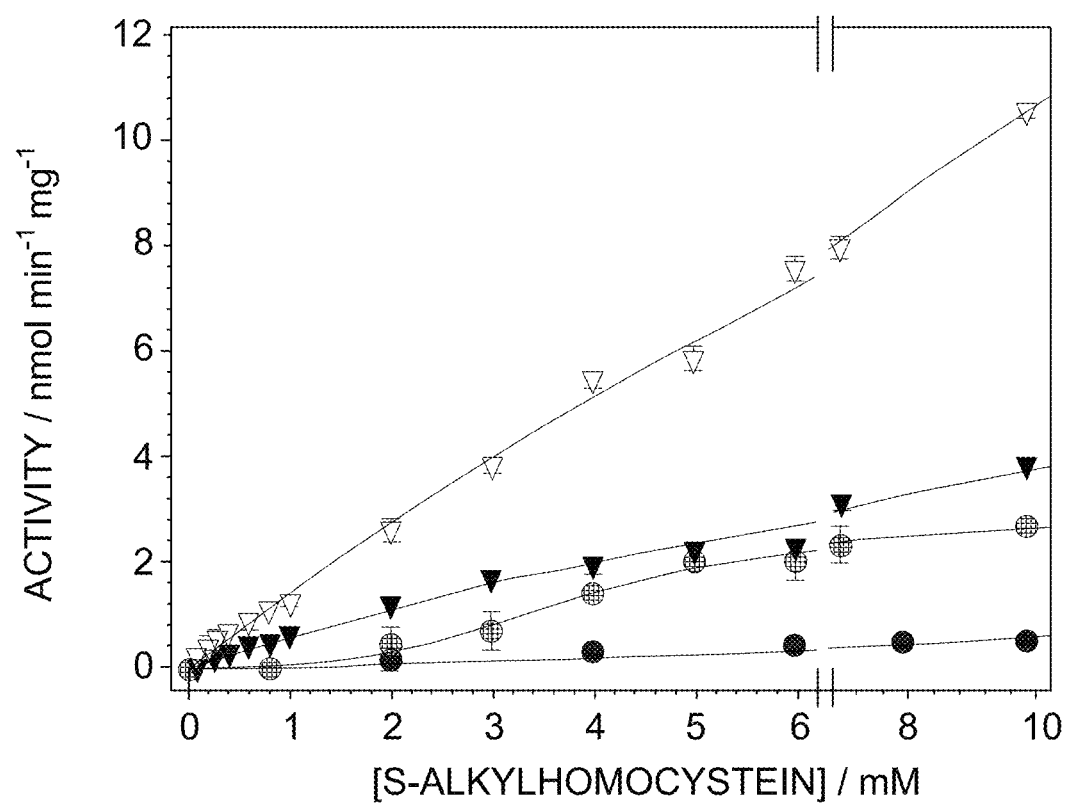

To further probe the role of the proximate isoleucine residue I105 in substrate recognition, the variants I105V/I317A and I105A/I317A were generated. With increasing size of the active center of the enzymes, conversion of the natural substrate methionine (FIG. 3D, E) is progressively reduced. On the other hand, the variants prefer long-chain substrates. Compared to the wild-type enzyme (FIG. 3A), substrate specificity of the variant I105A/I317A (FIG. 3E) is inverted (S-n-propylhomocysteine>S-n-butylhomocysteine>ethionine>>methionine). Hence, steric effects play a major role in substrate conversion by SAMS enzymes, and selectivity for certain substrates can be engineered by exchange of two amino acid positions only.

Example 6

Synthesis of SAM Derivatives by SAM Synthase Variants

Figure 4A:
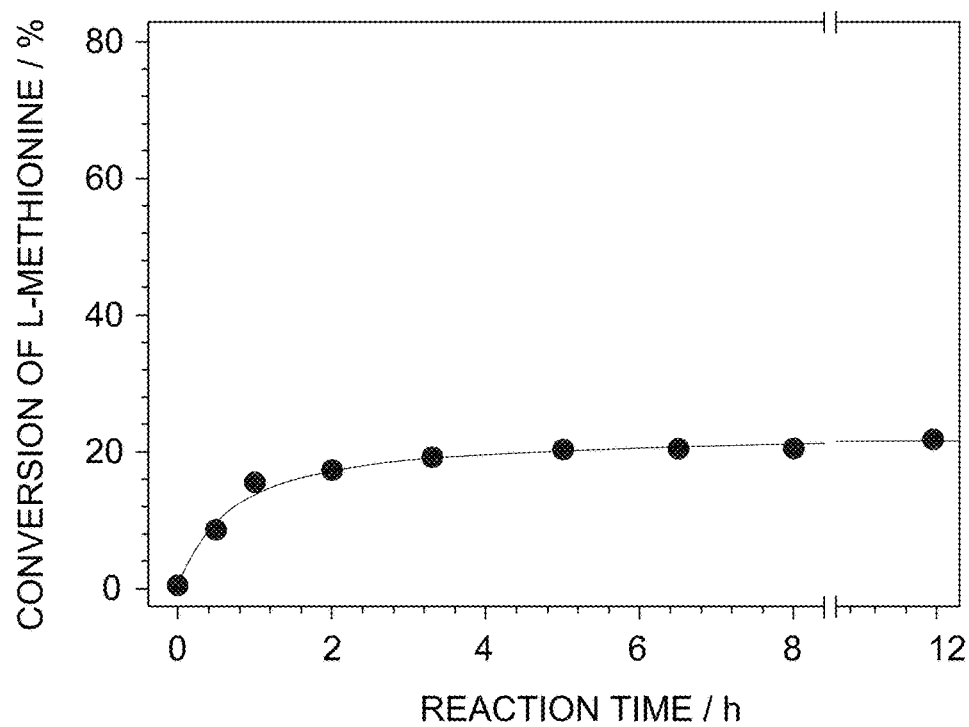
FIGS. 4A-4C: Formation of SAM and SAM Derivatives
Figure 4B:
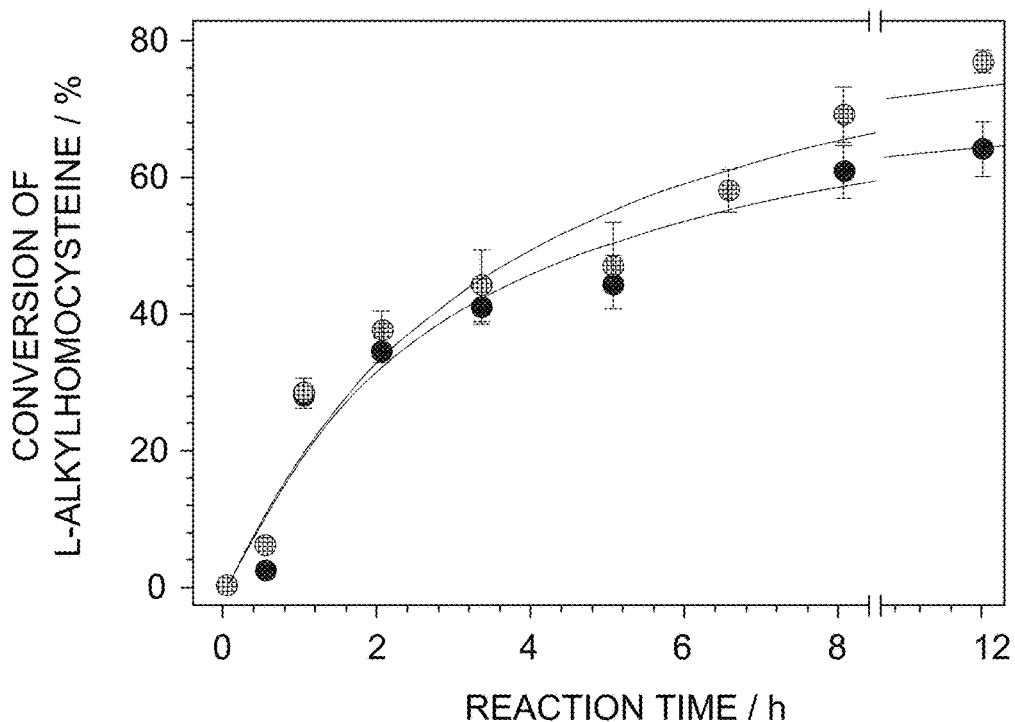
Figure 4C:
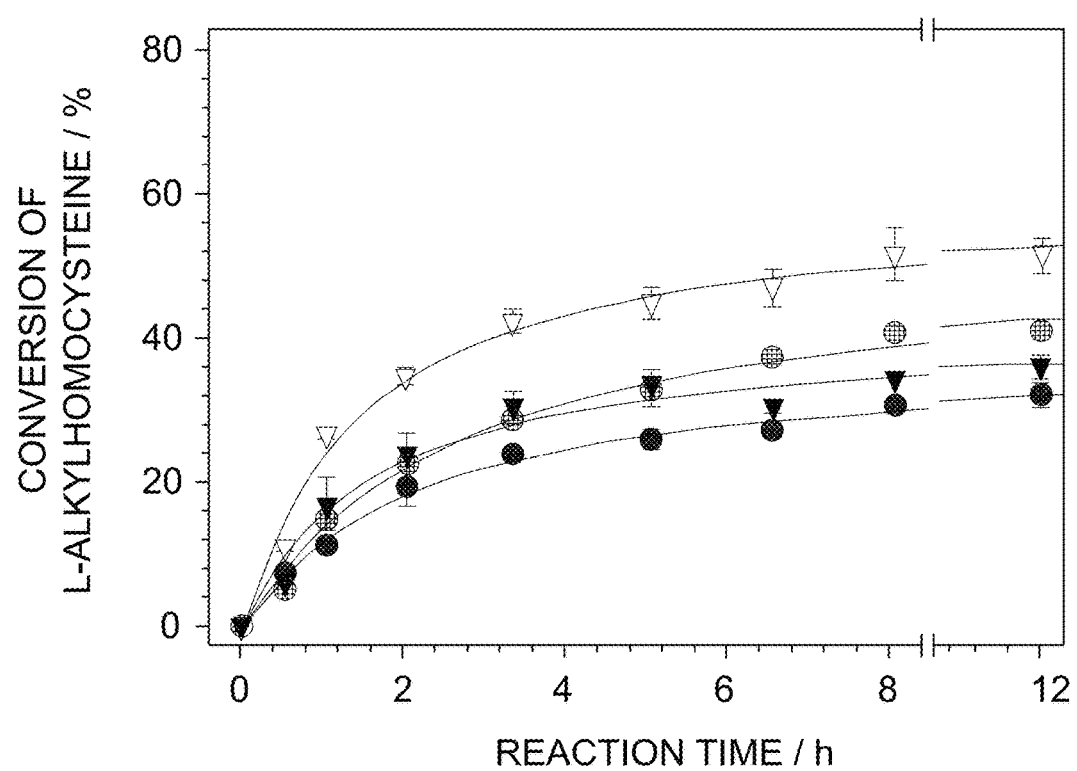

The suitability of the wild-type protein and of variants with appropriate substrate specificity (I317V and I317A) for the synthesis of SAM and analogues was evaluated by high-performance thin-layer chromatography. Since the enzymes were not inhibited by the D-enantiomer of the amino acid substrates, methionine and its derivatives could be advantageously applied as racemic mixture of its stereoisomeres in these reactions. The time course of SAM formation by the wild-type enzyme is shown in FIG. 4A. As described for several other SAMS proteins, the enzyme is inhibited by its product SAM which results in stagnating conversion and low yield. In contrast, this product inhibition is completely reduced in the variant I317V (FIG. 4B) and less pronounced in case of the mutant enzyme I317A (FIG. 4C). Accordingly, transformation of methionine and ethionine by SAMS-I317V in preparative synthetic reactions led to high conversion rates for the amino acid substrates. The syntheses were performed similar to the kinetic experiments but in larger scale (200 µmol). After prolonged incubation (18 hours) to reach maximum product yield, 84 and 89% of the L-amino acid was converted. In the production of the n-propyl- and n-butyl analogues of SAM by the variant I317A, 43% and 28% of conversion could be reached after 8 hours of reaction time. After product purification by cation exchange chromatography on SP-Sephadex C-25, SAM and its homologs could be recovered in final yields of 25, 17, 8 and 11%, respectively. As proven by $^1$H NMR, the enzymatically produced SAM contained a high excess ($\geq 90\%$) of the biologically active (S,S)-epimer. Interestingly, preparations of the S-adenosyl-L-ethionine, -propionine and -buthionine were racemic with respect to the chiral sulfonium center, which might be caused by faster racemization under the strongly acidic conditions in column purification.

Example 7

Kinetic Parameters for the Conversion of S-Alkylhomocysteines

The kinetic parameters for the conversion of S-alkylhomocysteines by *Bacillus subtitlis* SAM synthase and its variants as shown in Table 1 were calculated from the conversion rates of methionine and analogues as a function of the substrate concentration (FIGS. 2A-2C) which were determined by the standard SAM synthase assay known in the art, i.e. by photometric detection of the cleaved phosphate.

TABLE 1

| Enzyme | Substrate | $S_{0.5}$ (mM) | $V_{max}$ (nmol min$^{-1}$ mg$^{-1}$) | h |
|---|---|---|---|---|
| Wild-type | L-methionine | 1.04 ± 0.14 | 93.2 ± 3.1 | 1.1 ± 0.1 |
| | D,L-methionine | 1.92 ± 0.12 | 90.8 ± 1.6 | 1.7 ± 0.2 |
| | D,L-methionine-(methyl-D$_3$) | 1.86 ± 0.07 | 79.8 ± 2.3 | 2.2 ± 0.2 |
| I317V | L-methionine | 0.72 ± 0.04 | 408.0 ± 7.7 | 1.2 ± 0.1 |
| | D,L-methionine | 1.71 ± 0.12 | 446.2 ± 13.8 | 1.3 ± 0.1 |
| | D,L-ethionine | 10.94 ± 2.70 | 51.2 ± 9.1 | 1.3 ± 0.1 |
| I317A | L-methionine | 0.46 ± 0.02 | 34.8 ± 0.5 | 1.3 ± 0.1 |
| | D,L-methionine | 0.92 ± 0.05 | 37.7 ± 0.8 | 1.1 ± 0.1 |
| | D,L-ethionine | 2.99 ± 0.23 | 44.1 ± 1.6 | 1.2 ± 0.1 |
| | S-n-propyl-D,L-homocysteine | 0.90 ± 0.05 | 34.2 ± 0.7 | 1.1 ± 0.1 |
| | S-n-butyl-D,L-homocysteine | 3.56 ± 0.45 | 35.4 ± 2.6 | 1.4 ± 0.1 |
| | S-(2-methylvinyl)-D,L-homocysteine | 0.79 ± 0.04 | 22.4 ± 0.4 | 1.2 ± 0.1 |
| I105V/I317A | D,L-methionine | 3.77 ± 1.02 | 17.0 ± 2.0 | 1.0 ± 0.1 |
| | D,L-ethionine | 4.25 ± 0.20 | 5.7 ± 0.3 | 4.6 ± 0.8 |
| | S-n-propyl-D,L-homocysteine | 1.86 ± 0.41 | 17.7 ± 1.5 | 1.0 ± 0.1 |
| | S-n-butyl-D,L-homocysteine | 4.20 ± 0.41 | 11.9 ± 0.9 | 2.0 ± 0.2 |
| I105A/I317A | D,L-methionine | n.d. | 0.8 ± 0.2 | n.d |
| | D,L-ethionine | 3.91 ± 0.27 | 3.0 ± 1.8 | 2.9 ± 0.4 |
| | S-n-propyl-D,L-homocysteine | =10.0 | =10.8 ± 0.1 | 1.0 ± 0.1 |
| | S-n-butyl-D,L-homocysteine | =10.0 | =4.0 ± 0.2 | 0.8 ± 0.1 | n.d. not determined

What is claimed is:

1. An isolated polypeptide derived from wildtype *Bacillus subtilis* S-Adenosylmethionine (SAM) synthase or from a biologically active fragment thereof, comprising the amino acid sequence of SEQ ID NO: 2, SEQ ID NO: 3, SEQ ID NO: 4, SEQ ID NO: 5, SEQ ID NO:6 or SEQ ID NO:7.

2. An isolated nucleic acid encoding a polypeptide according to claim 1.

3. A vector comprising the nucleic acid of claim 2.

4. A host cell comprising the nucleic acid of claim 2.

5. A method for the biocatalytic generation of S-Adenosylmethionine (SAM) and/or SAM analogues having artificial alkyl chains or allyl chains, or chains of the type $-(CH_2)_n-OR$, $-(CH_2)_n-SR$, or $-(CH_2)_n-Hal$, wherein n is 1 to 3, R is an alkyl, and Hal is a halogen, comprising the step of reacting a suitable S-alkyl homocysteine, S-methylvinyl homocysteine, or other homocysteine derivative with a polypeptide of claim 1.

6. A host cell comprising the vector of claim 3.

* * * * *

SEQUENCE LISTING

<160> NUMBER OF SEQ ID NOS: 7

<210> SEQ ID NO 1
<211> LENGTH: 400
<212> TYPE: PRT
<213> ORGANISM: Bacillus subtilis

<400> SEQUENCE: 1

```
Met Ser Lys Asn Arg Arg Leu Phe Thr Ser Glu Ser Val Thr Glu Gly
1               5                   10                  15

His Pro Asp Lys Ile Cys Asp Gln Ile Ser Asp Ser Ile Leu Asp Glu
                20                  25                  30

Ile Leu Lys Lys Asp Pro Asn Ala Arg Val Ala Cys Glu Thr Ser Val
            35                  40                  45

Thr Thr Gly Leu Val Leu Val Ser Gly Glu Ile Thr Thr Ser Thr Tyr
50                  55                  60

Val Asp Ile Pro Lys Thr Val Arg Gln Thr Ile Lys Glu Ile Gly Tyr
65                  70                  75                  80

Thr Arg Ala Lys Tyr Gly Phe Asp Ala Glu Thr Cys Ala Val Leu Thr
                85                  90                  95

Ser Ile Asp Glu Gln Ser Ala Asp Ile Ala Met Gly Val Asp Gln Ala
            100                 105                 110

Leu Glu Ala Arg Glu Gly Thr Met Ser Asp Glu Glu Ile Glu Ala Ile
        115                 120                 125

Gly Ala Gly Asp Gln Gly Leu Met Phe Gly Tyr Ala Cys Asn Glu Thr
130                 135                 140

Lys Glu Leu Met Pro Leu Pro Ile Ser Leu Ala His Lys Leu Ala Arg
145                 150                 155                 160

Arg Leu Ser Glu Val Arg Lys Glu Asp Ile Leu Pro Tyr Leu Arg Pro
                165                 170                 175

Asp Gly Lys Thr Gln Val Thr Val Glu Tyr Asp Glu Asn Asn Lys Pro
            180                 185                 190

Val Arg Ile Asp Ala Ile Val Ile Ser Thr Gln His His Pro Glu Ile
        195                 200                 205

Thr Leu Glu Gln Ile Gln Arg Asn Ile Lys Glu His Val Ile Asn Pro
210                 215                 220

Val Val Pro Glu Glu Leu Ile Asp Glu Glu Thr Lys Tyr Phe Ile Asn
225                 230                 235                 240
```

```
Pro Thr Gly Arg Phe Val Ile Gly Gly Pro Gln Gly Asp Ala Gly Leu
                245                 250                 255

Thr Gly Arg Lys Ile Ile Val Asp Thr Tyr Gly Gly Tyr Ala Arg His
            260                 265                 270

Gly Gly Gly Ala Phe Ser Gly Lys Asp Ala Thr Lys Val Asp Arg Ser
        275                 280                 285

Ala Ala Tyr Ala Ala Arg Tyr Val Ala Lys Asn Ile Val Ala Ala Glu
    290                 295                 300

Leu Ala Asp Ser Cys Glu Val Gln Leu Ala Tyr Ala Ile Gly Val Ala
305                 310                 315                 320

Gln Pro Val Ser Ile Ser Ile Asn Thr Phe Gly Ser Gly Lys Ala Ser
                325                 330                 335

Glu Glu Lys Leu Ile Glu Val Val Arg Asn Asn Phe Asp Leu Arg Pro
            340                 345                 350

Ala Gly Ile Ile Lys Met Leu Asp Leu Arg Arg Pro Ile Tyr Lys Gln
        355                 360                 365

Thr Ala Ala Tyr Gly His Phe Gly Arg His Asp Val Asp Leu Pro Trp
    370                 375                 380

Glu Arg Thr Asp Lys Ala Glu Gln Leu Arg Lys Glu Ala Leu Gly Glu
385                 390                 395                 400

<210> SEQ ID NO 2
<211> LENGTH: 400
<212> TYPE: PRT
<213> ORGANISM: Artificial Sequence
<220> FEATURE:
<223> OTHER INFORMATION: mutant SAM synthase

<400> SEQUENCE: 2

Met Ser Lys Asn Arg Arg Leu Phe Thr Ser Glu Ser Val Thr Glu Gly
1               5                   10                  15

His Pro Asp Lys Ile Cys Asp Gln Ile Ser Asp Ser Ile Leu Asp Glu
                20                  25                  30

Ile Leu Lys Lys Asp Pro Asn Ala Arg Val Ala Cys Glu Thr Ser Val
            35                  40                  45

Thr Thr Gly Leu Val Leu Val Ser Gly Glu Ile Thr Thr Ser Thr Tyr
    50                  55                  60

Val Asp Ile Pro Lys Thr Val Arg Gln Thr Ile Lys Glu Ile Gly Tyr
65                  70                  75                  80

Thr Arg Ala Lys Tyr Gly Phe Asp Ala Glu Thr Cys Ala Val Leu Thr
                85                  90                  95

Ser Ile Asp Glu Gln Ser Ala Asp Ile Ala Met Gly Val Asp Gln Ala
                100                 105                 110

Leu Glu Ala Arg Glu Gly Thr Met Ser Asp Glu Glu Ile Glu Ala Ile
            115                 120                 125

Gly Ala Gly Asp Gln Gly Leu Met Phe Gly Tyr Ala Cys Asn Glu Thr
        130                 135                 140

Lys Glu Leu Met Pro Leu Pro Ile Ser Leu Ala His Lys Leu Ala Arg
145                 150                 155                 160

Arg Leu Ser Glu Val Arg Lys Glu Asp Ile Leu Pro Tyr Leu Arg Pro
                165                 170                 175

Asp Gly Lys Thr Gln Val Thr Val Glu Tyr Asp Glu Asn Asn Lys Pro
            180                 185                 190

Val Arg Ile Asp Ala Ile Val Ile Ser Thr Gln His His Pro Glu Ile
        195                 200                 205
```

```
Thr Leu Glu Gln Ile Gln Arg Asn Ile Lys Glu His Val Ile Asn Pro
210                 215                 220

Val Val Pro Glu Glu Leu Ile Asp Glu Thr Lys Tyr Phe Ile Asn
225                 230                 235                 240

Pro Thr Gly Arg Phe Val Ile Gly Gly Pro Gln Gly Asp Ala Gly Leu
                245                 250                 255

Thr Gly Arg Lys Ile Ile Val Asp Thr Tyr Gly Gly Tyr Ala Arg His
            260                 265                 270

Gly Gly Gly Ala Phe Ser Gly Lys Asp Ala Thr Lys Val Asp Arg Ser
                275                 280                 285

Ala Ala Tyr Ala Ala Arg Tyr Val Ala Lys Asn Ile Val Ala Ala Glu
290                 295                 300

Leu Ala Asp Ser Cys Glu Val Gln Leu Ala Tyr Ala Ala Gly Val Ala
305                 310                 315                 320

Gln Pro Val Ser Ile Ser Ile Asn Thr Phe Gly Ser Gly Lys Ala Ser
                325                 330                 335

Glu Glu Lys Leu Ile Glu Val Val Arg Asn Asn Phe Asp Leu Arg Pro
                340                 345                 350

Ala Gly Ile Ile Lys Met Leu Asp Leu Arg Arg Pro Ile Tyr Lys Gln
                355                 360                 365

Thr Ala Ala Tyr Gly His Phe Gly Arg His Ala Val Asp Leu Pro Trp
370                 375                 380

Glu Arg Thr Asp Lys Ala Glu Gln Leu Arg Lys Glu Ala Leu Gly Glu
385                 390                 395                 400
```

<210> SEQ ID NO 3
<211> LENGTH: 400
<212> TYPE: PRT
<213> ORGANISM: Artificial Sequence
<220> FEATURE:
<223> OTHER INFORMATION: mutant SAM synthase

<400> SEQUENCE: 3

```
Met Ser Lys Asn Arg Arg Leu Phe Thr Ser Glu Ser Val Thr Glu Gly
1               5                   10                  15

His Pro Asp Lys Ile Cys Asp Gln Ile Ser Asp Ser Ile Leu Asp Glu
                20                  25                  30

Ile Leu Lys Lys Asp Pro Asn Ala Arg Val Ala Cys Glu Thr Ser Val
                35                  40                  45

Thr Thr Gly Leu Val Leu Val Ser Gly Glu Ile Thr Thr Ser Thr Tyr
50                  55                  60

Val Asp Ile Pro Lys Thr Val Arg Gln Thr Ile Lys Glu Ile Gly Tyr
65                  70                  75                  80

Thr Arg Ala Lys Tyr Gly Phe Asp Ala Glu Thr Cys Ala Val Leu Thr
                85                  90                  95

Ser Ile Asp Glu Gln Ser Ala Asp Ile Ala Met Gly Val Asp Gln Ala
                100                 105                 110

Leu Glu Ala Arg Glu Gly Thr Met Ser Asp Glu Glu Ile Glu Ala Ile
                115                 120                 125

Gly Ala Gly Asp Gln Gly Leu Met Phe Gly Tyr Ala Cys Asn Glu Thr
130                 135                 140

Lys Glu Leu Met Pro Leu Pro Ile Ser Leu Ala His Lys Leu Ala Arg
145                 150                 155                 160

Arg Leu Ser Glu Val Arg Lys Glu Asp Ile Leu Pro Tyr Leu Arg Pro
                165                 170                 175
```

```
Asp Gly Lys Thr Gln Val Thr Val Glu Tyr Asp Glu Asn Asn Lys Pro
            180                 185                 190

Val Arg Ile Asp Ala Ile Val Ile Ser Thr Gln His His Pro Glu Ile
195                 200                 205

Thr Leu Glu Gln Ile Gln Arg Asn Ile Lys Glu His Val Ile Asn Pro
    210                 215                 220

Val Val Pro Glu Glu Leu Ile Asp Glu Thr Lys Tyr Phe Ile Asn
225                 230                 235                 240

Pro Thr Gly Arg Phe Val Ile Gly Gly Pro Gln Gly Asp Ala Gly Leu
                245                 250                 255

Thr Gly Arg Lys Ile Ile Val Asp Thr Tyr Gly Gly Tyr Ala Arg His
            260                 265                 270

Gly Gly Gly Ala Phe Ser Gly Lys Asp Ala Thr Lys Val Asp Arg Ser
    275                 280                 285

Ala Ala Tyr Ala Ala Arg Tyr Val Ala Lys Asn Ile Val Ala Ala Glu
            290                 295                 300

Leu Ala Asp Ser Cys Glu Val Gln Leu Ala Tyr Ala Val Gly Val Ala
305                 310                 315                 320

Gln Pro Val Ser Ile Ser Ile Asn Thr Phe Gly Ser Gly Lys Ala Ser
                325                 330                 335

Glu Glu Lys Leu Ile Glu Val Val Arg Asn Asn Phe Asp Leu Arg Pro
            340                 345                 350

Ala Gly Ile Ile Lys Met Leu Asp Leu Arg Arg Pro Ile Tyr Lys Gln
    355                 360                 365

Thr Ala Ala Tyr Gly His Phe Gly Arg His Asp Val Asp Leu Pro Trp
370                 375                 380

Glu Arg Thr Asp Lys Ala Glu Gln Leu Arg Lys Glu Ala Leu Gly Glu
385                 390                 395                 400

<210> SEQ ID NO 4
<211> LENGTH: 400
<212> TYPE: PRT
<213> ORGANISM: Artificial Sequence
<220> FEATURE:
<223> OTHER INFORMATION: mutant SAM synthase

<400> SEQUENCE: 4

Met Ser Lys Asn Arg Arg Leu Phe Thr Ser Glu Ser Val Thr Glu Gly
1               5                   10                  15

His Pro Asp Lys Ile Cys Asp Gln Ile Ser Asp Ser Ile Leu Asp Glu
            20                  25                  30

Ile Leu Lys Lys Asp Pro Asn Ala Arg Val Ala Cys Glu Thr Ser Val
        35                  40                  45

Thr Thr Gly Leu Val Leu Val Ser Gly Glu Ile Thr Thr Ser Thr Tyr
    50                  55                  60

Val Asp Ile Pro Lys Thr Val Arg Gln Thr Ile Lys Glu Ile Gly Tyr
65                  70                  75                  80

Thr Arg Ala Lys Tyr Gly Phe Asp Ala Glu Thr Cys Ala Val Leu Thr
                85                  90                  95

Ser Ile Asp Glu Gln Ser Ala Asp Ala Ala Met Gly Val Asp Gln Ala
            100                 105                 110

Leu Glu Ala Arg Glu Gly Thr Met Ser Asp Glu Glu Ile Glu Ala Ile
        115                 120                 125

Gly Ala Gly Asp Gln Gly Leu Met Phe Gly Tyr Ala Cys Asn Glu Thr
    130                 135                 140
```

```
Lys Glu Leu Met Pro Leu Pro Ile Ser Leu Ala His Lys Leu Ala Arg
145                 150                 155                 160

Arg Leu Ser Glu Val Arg Lys Glu Asp Ile Leu Pro Tyr Leu Arg Pro
            165                 170                 175

Asp Gly Lys Thr Gln Val Thr Val Glu Tyr Asp Glu Asn Asn Lys Pro
            180                 185                 190

Val Arg Ile Asp Ala Ile Val Ile Ser Thr Gln His His Pro Glu Ile
            195                 200                 205

Thr Leu Glu Gln Ile Gln Arg Asn Ile Lys Glu His Val Ile Asn Pro
            210                 215                 220

Val Val Pro Glu Glu Leu Ile Asp Glu Thr Lys Tyr Phe Ile Asn
225                 230                 235                 240

Pro Thr Gly Arg Phe Val Ile Gly Gly Pro Gln Gly Asp Ala Gly Leu
            245                 250                 255

Thr Gly Arg Lys Ile Ile Val Asp Thr Tyr Gly Gly Tyr Ala Arg His
            260                 265                 270

Gly Gly Gly Ala Phe Ser Gly Lys Asp Ala Thr Lys Val Asp Arg Ser
            275                 280                 285

Ala Ala Tyr Ala Ala Arg Tyr Val Ala Lys Asn Ile Val Ala Ala Glu
            290                 295                 300

Leu Ala Asp Ser Cys Glu Val Gln Leu Ala Tyr Ala Ala Gly Val Ala
305                 310                 315                 320

Gln Pro Val Ser Ile Ser Asn Thr Phe Gly Ser Gly Lys Ala Ser
            325                 330                 335

Glu Glu Lys Leu Ile Glu Val Val Arg Asn Asn Phe Asp Leu Arg Pro
            340                 345                 350

Ala Gly Ile Ile Lys Met Leu Asp Leu Arg Arg Pro Ile Tyr Lys Gln
            355                 360                 365

Thr Ala Ala Tyr Gly His Phe Gly Arg His Asp Val Asp Leu Pro Trp
            370                 375                 380

Glu Arg Thr Asp Lys Ala Glu Gln Leu Arg Lys Glu Ala Leu Gly Glu
385                 390                 395                 400
```

<210> SEQ ID NO 5
<211> LENGTH: 400
<212> TYPE: PRT
<213> ORGANISM: Artificial Sequence
<220> FEATURE:
<223> OTHER INFORMATION: mutant SAM synthase

<400> SEQUENCE: 5

```
Met Ser Lys Asn Arg Arg Leu Phe Thr Ser Glu Ser Val Thr Glu Gly
1               5                   10                  15

His Pro Asp Lys Ile Cys Asp Gln Ile Ser Asp Ser Ile Leu Asp Glu
            20                  25                  30

Ile Leu Lys Lys Asp Pro Asn Ala Arg Val Ala Cys Glu Thr Ser Val
            35                  40                  45

Thr Thr Gly Leu Val Leu Val Ser Gly Glu Ile Thr Thr Ser Thr Tyr
        50                  55                  60

Val Asp Ile Pro Lys Thr Val Arg Gln Thr Ile Lys Glu Ile Gly Tyr
65                  70                  75                  80

Thr Arg Ala Lys Tyr Gly Phe Asp Ala Glu Thr Cys Ala Val Leu Thr
                85                  90                  95

Ser Ile Asp Glu Gln Ser Ala Asp Ala Ala Met Gly Val Asp Gln Ala
            100                 105                 110
```

```
Leu Glu Ala Arg Glu Gly Thr Met Ser Asp Glu Ile Glu Ala Ile
            115                 120                 125

Gly Ala Gly Asp Gln Gly Leu Met Phe Gly Tyr Ala Cys Asn Glu Thr
130                 135                 140

Lys Glu Leu Met Pro Leu Pro Ile Ser Leu Ala His Lys Leu Ala Arg
145                 150                 155                 160

Arg Leu Ser Glu Val Arg Lys Glu Asp Ile Leu Pro Tyr Leu Arg Pro
                165                 170                 175

Asp Gly Lys Thr Gln Val Thr Val Glu Tyr Asp Glu Asn Asn Lys Pro
            180                 185                 190

Val Arg Ile Asp Ala Ile Val Ile Ser Thr Gln His His Pro Glu Ile
        195                 200                 205

Thr Leu Glu Gln Ile Gln Arg Asn Ile Lys Glu His Val Ile Asn Pro
    210                 215                 220

Val Val Pro Glu Glu Leu Ile Asp Glu Glu Thr Lys Tyr Phe Ile Asn
225                 230                 235                 240

Pro Thr Gly Arg Phe Val Ile Gly Gly Pro Gln Gly Asp Ala Gly Leu
                245                 250                 255

Thr Gly Arg Lys Ile Ile Val Asp Thr Tyr Gly Gly Tyr Ala Arg His
            260                 265                 270

Gly Gly Gly Ala Phe Ser Gly Lys Asp Ala Thr Lys Val Asp Arg Ser
        275                 280                 285

Ala Ala Tyr Ala Ala Arg Tyr Val Ala Lys Asn Ile Val Ala Ala Glu
    290                 295                 300

Leu Ala Asp Ser Cys Glu Val Gln Leu Ala Tyr Ala Val Gly Val Ala
305                 310                 315                 320

Gln Pro Val Ser Ile Ser Ile Asn Thr Phe Gly Ser Gly Lys Ala Ser
                325                 330                 335

Glu Glu Lys Leu Ile Glu Val Val Arg Asn Asn Phe Asp Leu Arg Pro
            340                 345                 350

Ala Gly Ile Ile Lys Met Leu Asp Leu Arg Arg Pro Ile Tyr Lys Gln
        355                 360                 365

Thr Ala Ala Tyr Gly His Phe Gly Arg His Asp Val Asp Leu Pro Trp
    370                 375                 380

Glu Arg Thr Asp Lys Ala Glu Gln Leu Arg Lys Glu Ala Leu Gly Glu
385                 390                 395                 400

<210> SEQ ID NO 6
<211> LENGTH: 400
<212> TYPE: PRT
<213> ORGANISM: Artificial Sequence
<220> FEATURE:
<223> OTHER INFORMATION: mutant SAM synthase

<400> SEQUENCE: 6

Met Ser Lys Asn Arg Arg Leu Phe Thr Ser Glu Ser Val Thr Glu Gly
1               5                   10                  15

His Pro Asp Lys Ile Cys Asp Gln Ile Ser Asp Ser Ile Leu Asp Glu
            20                  25                  30

Ile Leu Lys Lys Asp Pro Asn Ala Arg Val Ala Cys Glu Thr Ser Val
        35                  40                  45

Thr Thr Gly Leu Val Leu Val Ser Gly Glu Ile Thr Thr Ser Thr Tyr
    50                  55                  60

Val Asp Ile Pro Lys Thr Val Arg Gln Thr Ile Lys Glu Ile Gly Tyr
65                  70                  75                  80
```

```
Thr Arg Ala Lys Tyr Gly Phe Asp Ala Glu Thr Cys Ala Val Leu Thr
                85                  90                  95

Ser Ile Asp Glu Gln Ser Ala Asp Val Ala Met Gly Val Asp Gln Ala
            100                 105                 110

Leu Glu Ala Arg Glu Gly Thr Met Ser Asp Glu Ile Glu Ala Ile
        115                 120                 125

Gly Ala Gly Asp Gln Gly Leu Met Phe Gly Tyr Ala Cys Asn Glu Thr
130                 135                 140

Lys Glu Leu Met Pro Leu Pro Ile Ser Leu Ala His Lys Leu Ala Arg
145                 150                 155                 160

Arg Leu Ser Glu Val Arg Lys Glu Asp Ile Leu Pro Tyr Leu Arg Pro
                165                 170                 175

Asp Gly Lys Thr Gln Val Thr Val Glu Tyr Asp Glu Asn Asn Lys Pro
            180                 185                 190

Val Arg Ile Asp Ala Ile Val Ile Ser Thr Gln His His Pro Glu Ile
        195                 200                 205

Thr Leu Glu Gln Ile Gln Arg Asn Ile Lys Glu His Val Ile Asn Pro
210                 215                 220

Val Val Pro Glu Glu Leu Ile Asp Glu Thr Lys Tyr Phe Ile Asn
225                 230                 235                 240

Pro Thr Gly Arg Phe Val Ile Gly Gly Pro Gln Gly Asp Ala Gly Leu
                245                 250                 255

Thr Gly Arg Lys Ile Ile Val Asp Thr Tyr Gly Gly Tyr Ala Arg His
            260                 265                 270

Gly Gly Gly Ala Phe Ser Gly Lys Asp Ala Thr Lys Val Asp Arg Ser
        275                 280                 285

Ala Ala Tyr Ala Ala Arg Tyr Val Ala Lys Asn Ile Val Ala Ala Glu
290                 295                 300

Leu Ala Asp Ser Cys Glu Val Gln Leu Ala Tyr Ala Ala Gly Val Ala
305                 310                 315                 320

Gln Pro Val Ser Ile Ser Ile Asn Thr Phe Gly Ser Gly Lys Ala Ser
                325                 330                 335

Glu Glu Lys Leu Ile Glu Val Val Arg Asn Asn Phe Asp Leu Arg Pro
            340                 345                 350

Ala Gly Ile Ile Lys Met Leu Asp Leu Arg Arg Pro Ile Tyr Lys Gln
        355                 360                 365

Thr Ala Ala Tyr Gly His Phe Gly Arg His Asp Val Asp Leu Pro Trp
370                 375                 380

Glu Arg Thr Asp Lys Ala Glu Gln Leu Arg Lys Glu Ala Leu Gly Glu
385                 390                 395                 400

<210> SEQ ID NO 7
<211> LENGTH: 400
<212> TYPE: PRT
<213> ORGANISM: Artificial Sequence
<220> FEATURE:
<223> OTHER INFORMATION: mutant SAM synthase

<400> SEQUENCE: 7

Met Ser Lys Asn Arg Arg Leu Phe Thr Ser Glu Ser Val Thr Glu Gly
1               5                   10                  15

His Pro Asp Lys Ile Cys Asp Gln Ile Ser Asp Ser Ile Leu Asp Glu
            20                  25                  30

Ile Leu Lys Lys Asp Pro Asn Ala Arg Val Ala Cys Glu Thr Ser Val
        35                  40                  45
```

```
Thr Thr Gly Leu Val Leu Val Ser Gly Glu Ile Thr Thr Ser Thr Tyr
    50              55                  60
Val Asp Ile Pro Lys Thr Val Arg Gln Thr Ile Lys Glu Ile Gly Tyr
65              70                  75                  80
Thr Arg Ala Lys Tyr Gly Phe Asp Ala Glu Thr Cys Ala Val Leu Thr
            85                  90                  95
Ser Ile Asp Glu Gln Ser Ala Asp Val Ala Met Gly Val Asp Gln Ala
            100                 105                 110
Leu Glu Ala Arg Glu Gly Thr Met Ser Asp Glu Glu Ile Glu Ala Ile
            115                 120                 125
Gly Ala Gly Asp Gln Gly Leu Met Phe Gly Tyr Ala Cys Asn Glu Thr
        130                 135                 140
Lys Glu Leu Met Pro Leu Pro Ile Ser Leu Ala His Lys Leu Ala Arg
145                 150                 155                 160
Arg Leu Ser Glu Val Arg Lys Glu Asp Ile Leu Pro Tyr Leu Arg Pro
                165                 170                 175
Asp Gly Lys Thr Gln Val Thr Val Glu Tyr Asp Glu Asn Asn Lys Pro
            180                 185                 190
Val Arg Ile Asp Ala Ile Val Ile Ser Thr Gln His His Pro Glu Ile
        195                 200                 205
Thr Leu Glu Gln Ile Gln Arg Asn Ile Lys Glu His Val Ile Asn Pro
    210                 215                 220
Val Val Pro Glu Glu Leu Ile Asp Glu Glu Thr Lys Tyr Phe Ile Asn
225                 230                 235                 240
Pro Thr Gly Arg Phe Val Ile Gly Gly Pro Gln Gly Asp Ala Gly Leu
                245                 250                 255
Thr Gly Arg Lys Ile Ile Val Asp Thr Tyr Gly Gly Tyr Ala Arg His
            260                 265                 270
Gly Gly Gly Ala Phe Ser Gly Lys Asp Ala Thr Lys Val Asp Arg Ser
        275                 280                 285
Ala Ala Tyr Ala Ala Arg Tyr Val Ala Lys Asn Ile Val Ala Ala Glu
    290                 295                 300
Leu Ala Asp Ser Cys Glu Val Gln Leu Ala Tyr Ala Val Gly Val Ala
305                 310                 315                 320
Gln Pro Val Ser Ile Ser Ile Asn Thr Phe Gly Ser Gly Lys Ala Ser
                325                 330                 335
Glu Glu Lys Leu Ile Glu Val Val Arg Asn Asn Phe Asp Leu Arg Pro
            340                 345                 350
Ala Gly Ile Ile Lys Met Leu Asp Leu Arg Arg Pro Ile Tyr Lys Gln
        355                 360                 365
Thr Ala Ala Tyr Gly His Phe Gly Arg His Asp Val Asp Leu Pro Trp
    370                 375                 380
Glu Arg Thr Asp Lys Ala Glu Gln Leu Arg Lys Glu Ala Leu Gly Glu
385                 390                 395                 400
```